United States Patent [19]

Fagan et al.

[11] Patent Number: 5,425,744
[45] Date of Patent: Jun. 20, 1995

[54] OCCLUDER FOR REPAIR OF CARDIAC AND VASCULAR DEFECTS

[75] Inventors: Jack Fagan, Pepperell; L. Ven Raman, Framingham, both of Mass.; George Duval, Lake George, N.Y.; Gerry Ouellette, Framingham, Mass.

[73] Assignee: C. R. Bard, Inc., Murray Hill, N.J.

[21] Appl. No.: 229,140

[22] Filed: Apr. 18, 1994

Related U.S. Application Data

[63] Continuation of Ser. No. 60,680, May 10, 1993, abandoned, which is a continuation of Ser. No. 790,656, Nov. 5, 1991, abandoned.

[51] Int. Cl.$^6$ ............................................. A61B 17/00
[52] U.S. Cl. ............................ 606/213; 606/151; 606/215; 600/32; 128/887
[58] Field of Search ............... 606/213, 215, 151, 232, 606/220; 623/12; 600/32; 128/887, 899

[56] References Cited

U.S. PATENT DOCUMENTS

| | | | |
|---|---|---|---|
| 3,874,388 | 4/1975 | King | 606/232 |
| 4,007,743 | 2/1977 | Blake | 606/213 X |
| 4,027,677 | 6/1977 | Schulman | 128/785 |
| 4,112,952 | 9/1978 | Thomas et al. | 128/419 P X |
| 4,142,531 | 3/1979 | Magovern et al. | |
| 4,151,012 | 4/1979 | Simkovich et al. | 29/421.2 X |
| 4,917,089 | 4/1990 | Sideris | 606/153 X |

FOREIGN PATENT DOCUMENTS

| | | |
|---|---|---|
| 1146228 | 5/1983 | Canada. |
| 0159753 | 10/1985 | European Pat. Off.. |
| 2822603 | 11/1979 | Germany ............... 606/213 |
| 3116462 | 12/1982 | Germany ............... 606/213 |

OTHER PUBLICATIONS

Lock et al., "Transcatheter Closure of Atrial Septal Defects" Circulation vol. 79, No. 5, May 1989, pp. 1091–1098.
Elgiloy Brochure, Jun. 24, 1959, pp. 3–25.
Cubberly et al, Metals Handbook, vol. 3, p. 231, 1980.
Sims and Hagel, The Superalloys, 1990, pp. 161–165.
Bridges et al., Circulation, vol. 82, No. 5, Nov. 1990, pp. 1681–1689.
Hellenbrand et al., The Amer. Journal of Cardiology, Jul. 15, 1990, pp. 207–213.
Rome et al., Circulation, vol. 82, No. 6, Dec. 1990, pp. 751–758.
Bridges et al., Circulation, vol. 86, No. 6, Dec. 1992, pp. 1902–1908.

Primary Examiner—Stephen C. Pellegrino
Assistant Examiner—Jeffrey A. Schmidt
Attorney, Agent, or Firm—Morgan & Finnegan

[57] ABSTRACT

A device for the percutaneous transluminal repair of septal defects is disclosed. The device comprises first and second expandable occluders fastened to each other, each occluder including a framework having a central hub with elongated struts radiating therefrom. The struts are constructed such that they have a resistance to fatigue that exceeds the maximum fatigue stresses to which the struts will be subjected over a prolonged period in vivo. As such, the device exhibits a significantly decreased likelihood of metal fatigue failures after prolonged exposure in vivo.

80 Claims, 3 Drawing Sheets

OCCLUDER FOR REPAIR OF CARDIAC AND VASCULAR DEFECTS

This is a continuation of application Ser. No. 08/060,680, filed on May 10, 1993, abandoned which is a continuation of Ser. No. 07/790,656 filed on Nov. 5, 1991, abandoned.

FIELD OF THE INVENTION

The present invention relates to devices for the repair of intracardiac and vascular septal defects by percutaneous catheter placement of a corrective prosthetic device.

BACKGROUND OF THE INVENTION

Either congenitally or by acquisition, abnormal openings or holes can occur between adjacent chambers of the heart or its associated major blood vessels. Such openings are referred to, respectively, as interatrial and interventricular septal defects or patent ductus arteriosus and aortico-pulmonary windows. Such openings cause blood to leak from one chamber or artery to another and result in decreased pumping efficiency of the heart. Similarly, if defects occur in the Foramen Ovale, such defects, referred to as Patent Foramen Ovale (PFO), may result in a cerebral embolism. These deformities usually are congenital, however, they can also occur following a heart attack, significantly complicating subsequent coronary treatment and recovery. Such defects typically impose added strain on the heart and ultimately may lead to heart failure if not corrected.

Traditionally, such defects have required extensive open chest surgical techniques for correction. Specifically, the repair of such defects required an open heart procedure in which the heart was exposed and then opened and the defect was sewn shut by direct suturing. In connection therewith, a patch of a synthetic prosthetic material such as Dacron, Teflon, silk, nylon or pericardium was used to repair the defect.

Although other methods of occluding defects, most notably the use of a plastic plug to occlude the defect, were suggested as early as the 1950s, such methods similarly require the use of open heart surgery to access the defect and place the prosthetic implant.

Beginning in the early 1970s, a number of devices and methods were proposed for the percutaneous transluminal catheterization procedure for the repair of intracardiac defects. For example, U.S. Pat. No. 3,874,388 to King, et al., describes a device in which a pair of umbrella-like occluders are positioned on opposite sides of a defect and drawn and locked together at a central hub which crosses the defect. The device is said to effectively occlude the defect. Although the King device and method proposed to eliminate the need to perform open heart surgery, its use and structure were very complicated in that generally they required the umbrella-like occluders to be opened manually once positioned at the defect.

Similarly, U.S. Pat. No. 4,007,743 to Blake relates to an umbrella-like defect closure device having a plurality of elongated struts pivotally mounted to a central hub. Each pair of adjacent struts is interconnected by a strip formed of a foldable, resilient material which serves to automatically and resiliently open each umbrella-like element once such element is released from a protective sheath. As in the King patent, the device includes two separate occluders which are locked together by a snap connection once each of the occluder segments has been individually positioned across the septal defect.

Still another defect closure device is described in U.S. Pat. No. 4,917,089 to Sideris. The Sideris patent relates to an apparatus and method for transvenous closure of a septal perforation in the heart. The closure apparatus comprises an occluder which is positioned on the distal side of the perforation and an occluder-holder which is positioned on the proximal side of the perforation and is connected to the occluder across the perforation by means of a so-called "button" closure. As in the earlier transluminally delivered occluders, the Sideris patent requires that device elements positioned on opposite sides of a septal defect are separately delivered to the site of the defect and connected to one another in situ.

In U.S. Patent application Ser. No. 08/227,585, which is a continuation of Ser. No. 07/787,940, now abandoned, which corresponds to published European Application No. 0545091A2 entitled "Occluder and Method for Repair of Cardiac and Vascular Defects" attempts to overcome problems associated with the aforementioned devices are described. The application describes a device having separate occlusion elements that are connected in a manner such that they may be oriented in aligned or nonaligned relationships across the defect. Such a device is particularly useful in the repair of tunnel-like defects or defects having a non-uniform wall thickness. The application also describes a device having occlusion elements that are fluoroscopically distinguishable from one another, thereby enhancing the ability of a physician to visualize the device fluoroscopically during a percutaneous, transluminal placement procedure.

The devices of the application described above typically comprise a series of elongated struts attached at a central point and having two flexural pivot points thereon. For example, in one embodiment, each elongated strut includes a first coil located on the strut at a position adjacent to a central portion of the device, (referred to as a "shoulder" hinge), and a second coil located on the strut at a position remote from the shoulder, (referred to as an "elbow" hinge). Despite the numerous advantages associated with the occluders described in the application above, on occasion such devices may fail as a result of stress or fatigue after a limited time in vivo. In particular, failures have occurred on the strut arm at the elbow hinge or at a region immediately adjacent thereto. Although such failures have resulted in no clinical problems, (since the occluder rapidly becomes encapsulated in tissue prior to the incidence of failure), it would be desirable to eliminate even the possibility of such failures as a means of eliminating a potential source of complications.

Accordingly, a need exists for a device for the occlusion of cardiac and vascular defects that can withstand the full range of stresses applied to the device over a prolonged period of time in an in vivo environment. In connection therewith, a need exists for a vascular occluder configured in a manner such that flexural stresses are minimized and distributed throughout the device in order to provide an occlusion device that will not undergo stress failures in vivo.

SUMMARY AND OBJECTS OF THE INVENTION

The present invention relates to an intracardiac shunt defect occlusion device characterized by having an enhanced resistance to failures caused by stress or fatigue. In particular, the invention relates to an intracardiac occlusion device that has been modified to reduce and/or more evenly distribute stresses that may arise in the device during movement of the heart. The resulting device has a structure having a resistance to fatigue exceeding the maximum fatigue stresses to which the device may be subjected during use.

Additionally, by selecting certain metallic alloy compositions for use in the device, the ability of the device to resist corrosion over an extended time in vivo can be enhanced. This resistance to corrosion is believed to further enhance the device in its ability to resist failure over prolonged use.

Numerous modifications can be used to achieve the desired results, and combinations of two or more of such modifications can be used as well. Among the modifications useful for reducing stresses are the following:

a) substitution of wire having a square, rectangular, trapezoidal or triangular cross section for cylindrical wires that are currently used in occluder devices, b) increasing the diameter of shoulder and elbow coils which constitute the flexural hinge points about which portions of the device may bend, c) substituting an alloy comprising nickel, cobalt, chromium and molybdenum for the stainless steel alloys currently used to form the device, d) adding an additional flexural hinge point (wrist coil) at a location distal to the elbow hinge point, and e) adding additional turns to coils constituting the flexural hinge points.

Additionally, when using the alloys described above the ultimate strength of the device can be further enhanced by annealing the framework of the device at a temperature of between about 450°1000° F. for several minutes. Such a process results in a precipitation hardening of the alloy, increasing both its strength and stiffness.

Thus, it is one object of the present invention to provide a septal defect occlusion device that has increased resistance to stress failures and fatigue over a prolonged period of time.

It is another object of the present invention to provide an occlusion device which reduces stresses that may occur therein.

It is a further object of the invention to provide a defect occlusion device which more evenly distributes stresses that may be contained therein.

It is yet another object of the present invention to provide a defect occlusion device having an inherent resistance to fatigue that exceeds the maximum fatigue stresses to which the device may be subjected over a prolonged period of time.

It is still a further object of the present invention to provide a defect occlusion device that can resist corrosion over a prolonged in vivo exposure.

Other objects and features of the present invention will become apparent from the following detailed description when taken in connection with the accompanying drawings which disclose multiple embodiments of the invention. It is to be understood that the drawings are designed for the purpose of illustration only, and are not intended as a definition of the limits of the invention.

DETAILED DESCRIPTION OF THE INVENTION

Figure 1:
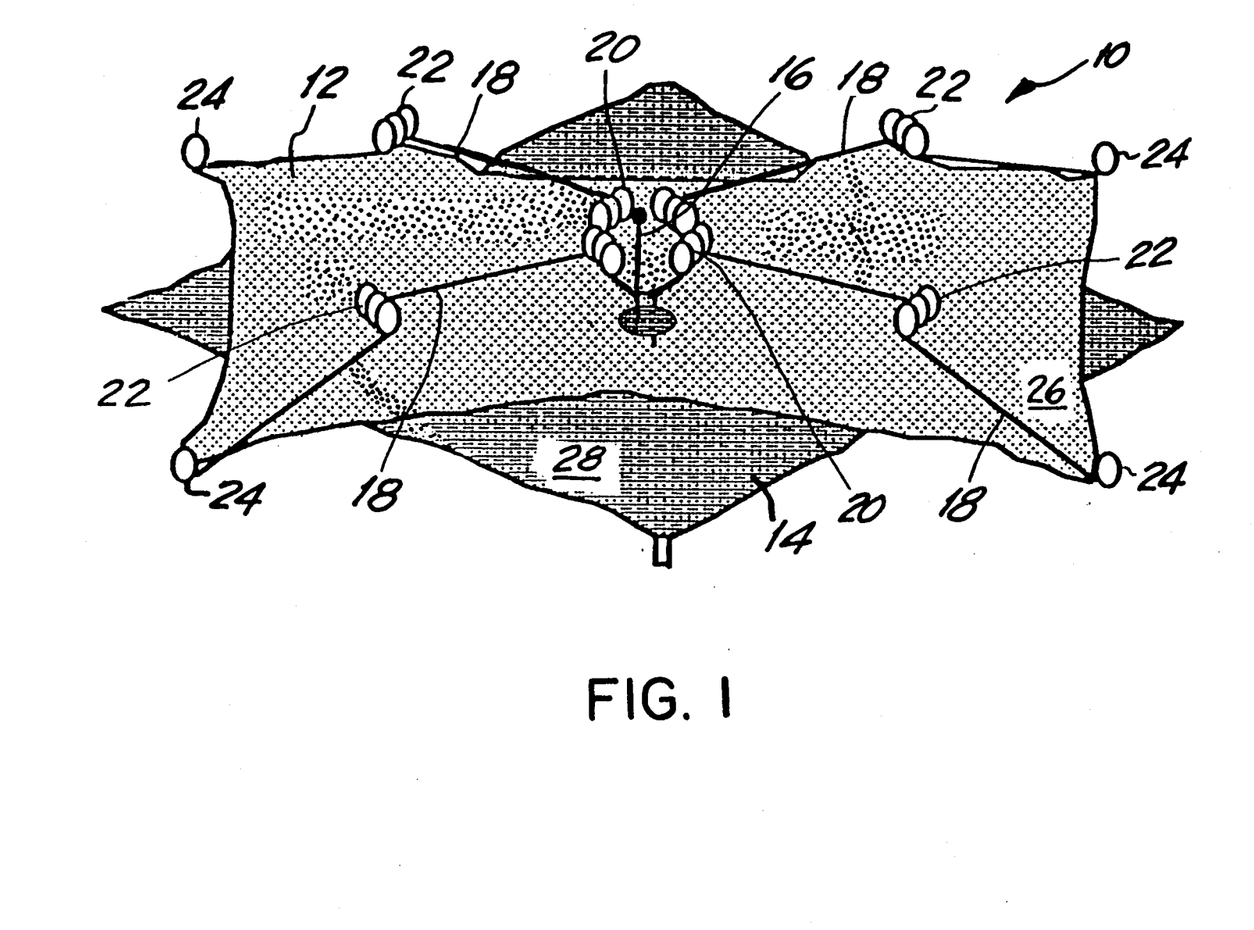
FIG. 1 is a schematic illustration of one type of occluder device known to the prior art.

FIG. 1 depicts an occlusion device of a type known in the prior art. As shown in FIG. 1, the device 10 comprises a first occluder 12 connected to a second occluder 14 in a face-to-face relationship. The occluders 12, 14 are connected to each other by means of a central hub or wire 16 which defines a central axis through each of the occluders 12, 14. It is noted that as used herein, the term "central axis" is not meant to imply that the wire or hub is necessarily positioned at the geometric center, if any, of its respective occluder. Rather, the term is intended to describe a reference line oriented in a perpendicular relationship to the plane of each occluder, the line passing through any given reference point on the occluder.

Each occluder comprises generally a framework formed by a plurality of elongated struts 18 which radiate from the central hub 16 of the occluder. The framework can be collapsed and then automatically opened by resilient means which are provided in each of the elongated struts. Specifically, each strut includes at least one flexural hinge point or shoulder 20 about which the elongated strut 18 may flex. Such shoulders are positioned adjacent to the central hub of each occluder.

In a collapsed configuration, the elongated struts 18 are pivotally flexed about the shoulders 20 to cause the struts to be oriented in a position that is generally parallel to the central axis of the occluder defined by the hub or the wire 16. The struts are maintained in this position against resilient forces by enclosing the device within a tubular sheath at the distal end of a delivery catheter which maintains the device in a collapsed configuration. Upon withdrawal of the sheath during the placement procedure, resilient forces stored within the elongated struts at the shoulders 20 cause the device to spring open by pivoting the struts about the hinge points defined by the shoulders. The struts 18 open to an orientation generally perpendicular to the central axis of the occluder.

The struts 18 include a second flexural hinge point or elbow 22 to provide a point on each strut about which the strut arm itself can fold, thereby allowing the length of the strut in its folded configuration to be shortened. In addition, the elbows serve as a location at which the struts may be preferentially bent in order to absorb stresses that may develop during movement of the septal wall in which the device is positioned as a result of the heart's natural rhythm.

Each strut preferably also includes a loop 24 at its distal end to conceal sharp areas that might otherwise damage tissue during insertion and placement of the device.

Attached to the strut frameworks are patches 26, 28 which, when the device is deployed, cover and occlude the shunt defect. Although numerous biocompatible materials can be used as the patch material, a material such as Dacron is typically used. Among the necessary characteristics of the patch material are biocompatibility and resistance to fluid transfer across the material. The material must be such that these properties can be maintained for extended periods in vivo. Additionally, the patch material must be flexible to allow the occluder device to be folded and compressed within a sheath prior to and during delivery to a predetermined location within a patient. An aperture 30 is formed within each of the patches 26, 28 and allows an interconnecting structure to connect the occluder elements to each other. The patches 26, 28 can be held to the strut framework by a plurality of stitches formed from sutures which encircle the struts and pass through the patch material.

Typically, occlusion devices of the above design employ 304V stainless steel wire having a circular cross-section and a diameter of approximately 0.010 inches to form the elongated struts or spring arms. In addition, each of the struts typically includes a shoulder 20 and an elbow 22, each of which comprise a coil having three turns. The inside diameter of the coils forming the shoulder hinge points is typically of the order of approximately 0.016 inches, and the inside diameter of the coils forming the elbow hinge points is typically of the order of approximately 0.012 inches.

Figure 2:
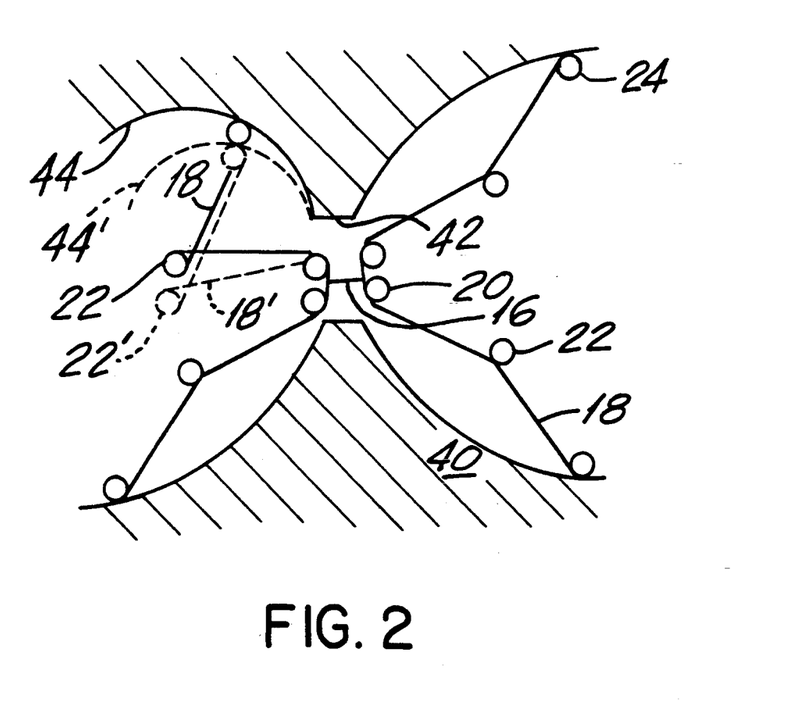
FIG. 2 is a schematic depiction of the cause of the stresses to which an occluder device can be subjected in vivo.

An occluder of the type depicted in FIG. 1 is shown schematically as deployed across a septal defect in FIG. 2. It is noted that, as depicted in FIG. 2, when positioned in vivo, the occluders often have at least one strut that becomes displaced toward the center of the device as a result of contraction of the heart chamber. Specifically, a septum 40 having a defect comprising an aperture defined by walls 42 has an occlusion device 10 positioned therein. During pumping of the heart, portions 44 of the septum deflect as well (shown in phantom 44') causing the strut 18 in contact with the septal portion 44 to deflect (shown in phantom 18').

The deflection is believed to cause stresses that become manifested as metal fatigue in the elbows 22, thereby resulting in a stressed condition in such elbows 22'. Over repeated cycles of bending and releasing, as occurs by the natural pumping action of the heart, the metal that forms the elbow becomes fatigued and causes failures to develop in the device. These failures occur typically at the elbow 22 or on the strut arm 18 at a location immediately adjacent to the elbow.

Figure 3:
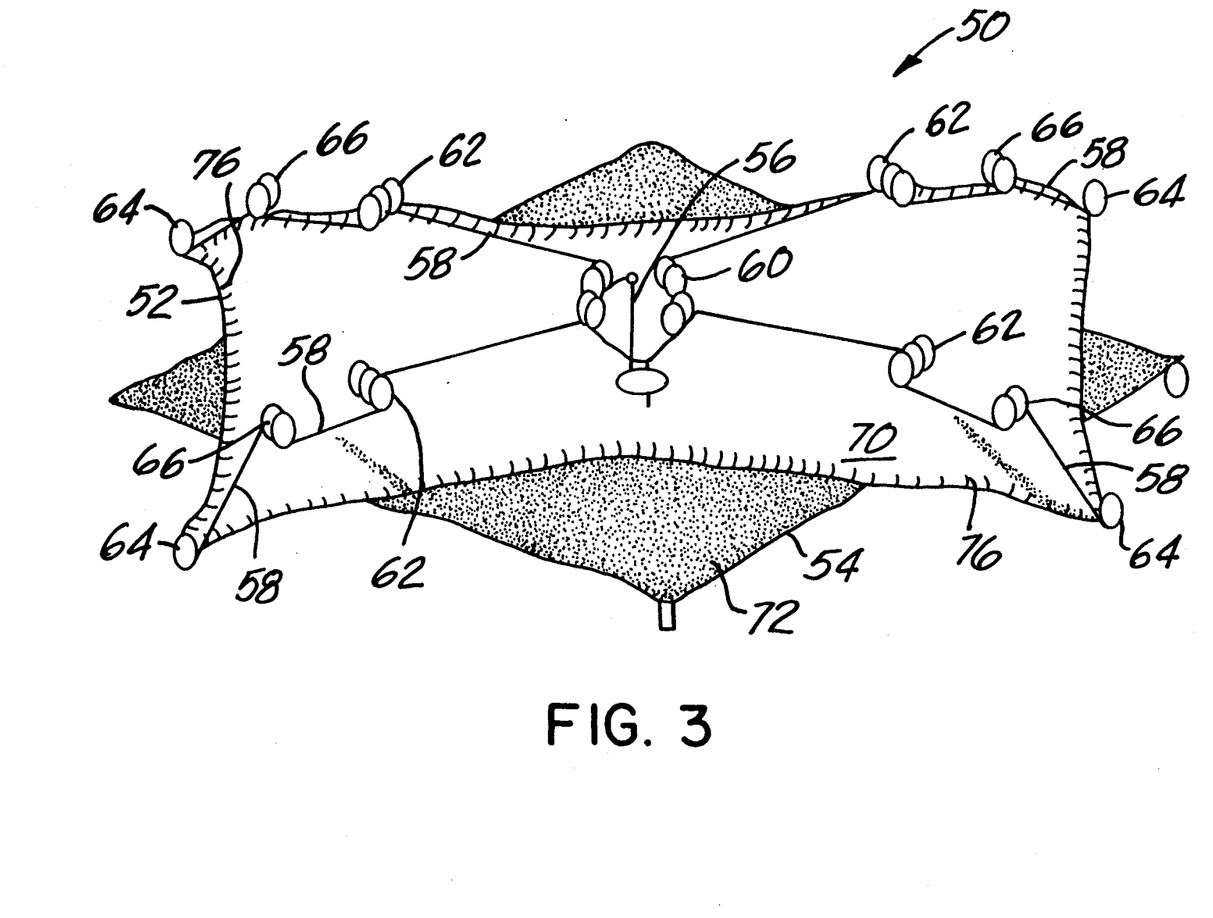
FIG. 3 is a schematic illustration of one embodiment of an occluder of the present invention.

One embodiment of an occlusion device having a reduced liklihood of metal fatigue failure at the elbow is depicted in FIG. 3. Such a device 50 comprises a pair of occluder elements 52, 54 connected to one another in a face-to-face relationship. The occluders 52, 54 are connected to each other by means of a central hub or wire 56 which defines a central axis through each of the occluders 52, 54. As in the device depicted in FIG. 1, the term "central axis" is intended only to describe a reference line oriented in a perpendicular relationship to the point of each occluder and passing through a given reference point on the occluder.

Each occluder includes a plurality of elongated struts 58 which radiate from the central hub and provide a framework for the occluder. As in the device described previously, the framework is adapted to be collapsed and then automatically opened by resilient means which are provided in each of the elongated struts 58. Specifically, each strut includes at least one flexural hinge point or shoulder 60 about which the elongated strut 58 may flex. In a collapsed configuration, the elongated struts 58 are pivotally flexed about the shoulders 60 to cause the struts to be oriented in a position that is generally parallel to the central axis of the occluder as defined by the hub or wire 56. The struts can be maintained in this position against resilient forces by enclosing the device with a tubular sheath located at the distal end of a delivery catheter which serves to maintain the device in a collapsed configuration. Upon withdrawal of the sheath during the placement procedure, resilient forces stored within the elongated struts at shoulders 60 cause the device to spring open resiliently by pivoting the struts about the shoulder. The struts 58 open to an orientation that is generally perpendicular to the central axis defined by the hub 56 of the occluder.

A second flexural hinge point or elbow 62 is provided on the strut 58 to further enhance operation of the occlusion device. As noted previously, the elbow provides a point about which the strut arm itself can fold, thereby allowing the length of the strut in its folded configuration to be shortened. Additionally, the elbows serve to absorb stresses which can be present within the framework of the device as a result of the natural motion of the heart.

Each strut preferably also includes a loop 64 at its outer end to conceal sharp areas that might otherwise cause damage to tissue during insertion and placement of the device.

As in the device shown in FIG. 1, attached to the strut frameworks are patches 70, 72 which, when the device is deployed, cover and occlude the septal defect. Numerous biocompatible materials including Teflon, silk, nylon and pericardium can be used as the patch material, however, a material such as Dacron is preferred. Among the necessary characteristics of the patch material are biocompatibility and resistance to fluid transfer across the material. The material must be such that these properties can be maintained for extended periods in vivo. Additionally, the patch material must be flexible to allow the occluder device to be folded and compressed within a sheath prior to and during delivery to a predetermined location within a patient.

An aperture 74 is formed within each of the patches 70, 72 and allows an interconnecting structure to connect the occluder elements to each other. The patches 70, 72 can be held to the strut framework by a plurality of stitches formed from sutures which encircle the struts and pass through the patch material.

In a preferred embodiment, the stitches attach to the patches to the framework at least at regions at which the shoulder and elbow hinge points 60, 62 and loops 64 contact the patch material. Alternatively, the sutures can be tied off at each loop and spiraled through the patch material and toward the central hub 56 terminating with knots tied to the hinge points. A ribbing 76 formed by a series of coarsely placed stitches is preferably formed along the peripheral edges of the patch material. The ribbing provides an area of increased patch material thickness and serves to provide a degree of stiffness and support to the outer edge of the patch material.

In the illustrative embodiment depicted in FIG. 3, each of the occluders 52, 54 is square. It is noted that the shape of the occluder elements is not intended to be limited as such. Rather, occluders having rectangular, circular or other geometries are contemplated as well and are intended to be encompassed within the scope of the invention.

Unlike the device depicted in FIG. 1, the device of FIG. 3 can include a third flexural hinge point or wrist 66 positioned on each strut 58 between the elbow 62 and the loop 64. The purpose of the wrist 66 is to reduce fatigue in the struts by absorbing and distributing stresses which can arise in the struts during natural movement of the heart. By providing an additional flexural point or coil in the form of a wrist 66 on each strut, the framework is provided with a means for distributing stresses more evenly, thereby reducing fatigue and significantly decreasing the possibility that failures can occur within the material forming the struts.

As noted previously, the present invention contemplates numerous ways by which stress and fatigue can be reduced in the occluder framework to effectively provide the device with infinite fatigue resistance. Thus, the device is expected to have a resistance to fatigue or stress failures which is greater than the maximum cumulative fatigue or stress to which the device will be subjected over the lifetime of the patient.

The specific modifications to the device for providing infinite fatigue and corrosion resistance include dimensional changes to the wire used to form the framework, changes to the diameter of the coils which comprise the shoulder and elbow of the framework, substitution of the metallic alloys used to form the framework structure, the addition of a third flexural hinge point (wrist) to the framework, variations in the number of turns in the flexural points, and any combination of the above improvements. Each of these is discussed separately below.

As discussed above, in the prior art the wire used to form the framework of the occluder elements was typically a wire having a circular cross section and a diameter of approximately 0.01 inches. In connection with the present invention, however, it has been found that if a wire having a square, rectangular, trapezoidal or triangular cross section of approximately 0.005–0.015 inches on edge, is substituted for the round wires of the prior art devices, stresses within the device can be reduced. For example, in the case in which a square wire having a cross section of approximately 0.008 inches is used to form the occluder framework, stresses within the device can be reduced by approximately 29%. If a wire having a rectangular cross section is used, a wire of approximately 0.007 inches by approximately 0.009 inches is preferred.

It should be noted, however, that it is not absolutely necessary that non-circular wire be used to form the device. Rather, wire having a circular cross section is contemplated as well. It is preferred that such a round wire have a diameter of approximately 0.009 inches.

The devices of the prior art have flexural hinge points, (the shoulder and elbow), which typically have been formed by wrapping the wire comprising the struts about mandrels. Typically, the mandrel used to form the shoulder coils has a diameter of approximately 0.016 inches, while the mandrel used to form the elbow coils has a diameter of approximately 0.012 inches. In connection with the invention, it has been found that if a mandrel having a diameter of approximately 0.010–0.025 inches is used to form both the shoulder and the elbow coils which form the flexural hinge points, stresses in the device can be reduced. In particular, if a mandrel having a diameter of approximately 0.016 inches is used to form the flexural hinge points, stresses in the occluder framework can be reduced by approximately 22%.

The material that has been used to form the framework for the occluders of the prior art was typically 304V stainless steel. In connection with the present invention, a metallic alloy such as MP35N available from Maryland Specialty Wire, Inc. (Cockeysville, Md. 21030) or a metallic alloy such as Elgiloy available from Elgiloy Company (Elgin, Ill. 60123) can be substituted. The substitution of the MP35N alloy for the 304V wire of the prior art has been found to provide the occluder with an increased stress capability of approximately 14%. In addition, the substitution of the MP35N metallic alloy for the 304V stainless steel of the prior art has been found to provide enhanced resistance to corrosion to the occcluders of the present invent on. The reduction or elimination of corrosion is believed to further decrease the possibility of device failure during prolonged exposure to an in vivo environment.

MP35N is a metallic alloy composition comprising approximately 35% nickel, 35% cobalt, 20% chromium, and approximately 9.75% molybdenum. The alloy is multiphase alloy that is face-centered-cubic (fcc) in the annealed condition and has a microstructure similar to that of austenitic stainless steel. When the alloy is cold-worked, such as when it is drawn to form a wire, the microstructure changes so that a portion of the fcc phase transforms to a hexagonal close-packed phase. This phase transformation results in an increase in the strength of the wire. A suitable degree of phase transformation is believed to occur for wires that have been cold-worked by drawing to result in a 30–80% reduction in cross-sectional area.

Additional strengthening of the wire can be obtained when a cold-worked structure, such as a drawn wire formed into an occluder framework, is subjected to an aging treatment at an elevated temperature. In connection therewith, heating the alloy for several minutes at a temperature in the range of approximately 450°–1000° F. causes a precipitation hardening of the alloy which increases both its strength and its stiffness.

Similarly, Elgiloy is a metallic alloy composition comprising 39–41% cobalt, 19–21% chromium, 14–16% nickel, 6–8% molybdenum, 1.5–2.5% manganese, 0–0.15% carbon, 0–0.1% beryllium and the balance comprising iron. Like MP35N, Elgiloy is preferred for use in the present invention due to its strength, stiffness, and resistance to structural failure under the conditions at which the occluder device is expected to be used.

Still another change is the addition of an extra spring coil (the wrist coil 66) as shown in FIG. 3. The use of a wrist coil 66 has been found to reduce stresses in the device by approximately 50% as a result of complimentary load sharing between the wrist, elbow and shoulder flexural points. It is preferred that the wrist coil have two turns and be formed on a mandrel having a diameter of approximately 0.010–0.025 inches. In this range, a diameter of approximately 0.016 inches is most preferred.

Finally, in some circumstances, it has been found desirable to vary the number of turns of the coils comprising the flexural points. For example, when each of the flexural hinge points comprises a coil having three turns, stresses in the wire framework have been found to decrease by approximately 50%.

As pointed out previously, the present invention is not necessarily intended to be limited to an occlusion device having only one of the features described above. Rather, the invention relates broadly to a device for percutaneous transluminal repair of septal defects in which the device comprises two occluders, each of which includes a plurality of struts having a resistance to fatigue that exceeds the maximum fatigue to which such struts may be subjected in vivo. Such a result can be achieved using the previously described improvements either alone or in various combinations with one another.

For example, in one preferred embodiment, the occlusion device includes two occluders each of which are formed of MP35N alloy in the form of 0.008 inch square wire. The wire is used to form an occluder framework having four struts, each of said struts including flexural hinge points defining a shoulder, an elbow and a wrist as well as a loop on the distal end of each strut. It is preferred that the shoulder and wrist hinge points be formed of coils each having two turns of wire and the elbow hinge point be formed of a coil having three turns of wire. The inside diameter of at least the wrist and shoulder coils are preferably about 0.016 inches. The inside diameter of the elbow coil may also be about 0.016 inches or, in the alternative, it can have a slightly smaller diameter of approximately 0.012 inches. As noted previously, once formed, the framework can be heated to a temperature of between approximately 450°-1000° F. for a period of time sufficient to cause precipitation hardening of the alloy forming the framework, thereby enhancing the strength and stiffness of the occluder.

Equivalents

Although the specific features of the invention are shown in some drawings and not in others, this is for convenience only, as each feature may be combined with any or all of the other features in accordance with the invention.

It should be understood, however, that the forgoing description of the invention is intended merely to be illustrative thereof, that the illustrative embodiments are presented by way of example only and that other modifications, embodiments, and equivalents may be apparent to those skilled in the art without departing from its spirit.

Having thus described the invention, what we desire to claim and secure by Letters Patent is:

1. A device for percutaneous transluminal repair of septal defects comprising:
    a first occluder having an initial cross sectional configuration smaller than that of the defect to be repaired and a second expanded configuration larger than that of the defect;
    a second occluder having an initial cross sectional configuration smaller than that of the defect to be repaired and a second expanded configuration larger than that of the defect; and
    a connector for fastening the first occluder to the second occluder;
    at least one of said first occluder or said second occluder including a framework comprising a central hub having a plurality of elongated struts radiating therefrom;
    wherein at least one of said struts has at least three flexural hinge points and at least one end loop, said flexural hinge points including a shoulder flexural hinge point, an elbow flexural hinge point and at least one flexural hinge point located between the end loop and the elbow flexural hinge point.

2. The device of claim 1 wherein said at least one elongated strut comprises a wire having a square, round, rectangular, trapezoidal or triangular cross section.

3. The device of claim 2 wherein said cross section is approximately 0.005-0015 inches on edge.

4. The device of claim 2 wherein said at least one elongated strut comprises a wire having a square cross section of approximately 0.008 inches on edge.

5. The device of claim 2 wherein said at least one elongated strut comprises a wire having a circular cross section of approximately 0.009 inches in diameter.

6. The device of claim 2 wherein said at least one elongated strut comprises a wire having a rectangular cross section of approximately 0.007 inches by approximately 0.009 inches.

7. The device of any one of claims 1 to 5 wherein said flexural hinge points comprise coiled portions of the elongated strut.

8. The device of claim 7 wherein said coiled portions have an inner diameter of approximately 0.010-0.025 inches.

9. The device of claim 7 wherein said coiled portions have an inner diameter of approximately 0.016 inches.

10. The device of claim 7 wherein said coiled portions include at least two coils.

11. The device of claim 7 wherein said coiled portions include at least three coils.

12. The device of claim 1 wherein said at least one elongated strut comprises a wire fabricated of a metallic alloy containing nickel, cobalt, chromium and molybdenum.

13. The device of claim 12 wherein said alloy comprises approximately 35% nickel, 35% cobalt, 20% chromium and 9.75% molybdenum.

14. The device of claim 12 wherein said alloy further comprises manganese, carbon, beryllium and iron.

15. The device of claim 14 wherein said alloy comprises at least approximately 14% nickel, 39% cobalt, 19% chromium, 6% molybdenum and 1.5% manganese.

16. The device of claim 15 wherein said alloy further comprises up to approximately 0.15% carbon and 0.1% beryllium.

17. The device of claim 12 wherein said alloy is annealed to a degree sufficient to cause precipitation hardening thereof.

18. The device of claim 17 wherein said annealing is carried out at a temperature between approximately 450°-1000° F.

19. The device of claim 12 wherein said wire has been cold-worked to reduce its cross-sectional area by approximately 30-80%.

20. A device for percutaneous transluminal repair of septal defects comprising:
    a first occluder having an initial cross sectional configuration smaller than that of the defect to be repaired and a second expanded configuration larger than that of the defect;
    a second occluder having an initial cross sectional configuration smaller than that of the defect to be repaired and a second expanded configuration larger than that of the defect; and
    a connector for fastening the first occluder to the second occluder;
    each of the first occluder and second occluder comprising a framework having a central hub with a plurality of elongated struts radiating therefrom;
    the framework fabricated of a wire having a square, rectangular, round, trapezoidal or triangular cross section and having a metallic alloy composition comprising nickel, cobalt, chromium and molybdenum;

each of said elongated struts further including three flexural hinge points and an end loop, said flexural hinge points including a shoulder flexural hinge point, an elbow flexural hinge point and a flexural hinge point located between the end loop and the elbow flexural hinge point.

21. The device of claim 20 wherein the metallic alloy composition is annealed to a degree sufficient to cause precipitation hardening thereof.

22. The device of claim 20 wherein the metallic alloy composition comprises an alloy selected from the group consisting of MP35N and Elgiloy.

23. The device of claim 20 wherein the flexural hinge points comprise coiled portions of the elongated strut.

24. The device of claim 20 wherein said cross section is approximately 0.005–0.015 inches on edge.

25. The device of claim 20 wherein said at least one elongated strut comprises a wire having a square cross section of approximately 0.008 inches on edge.

26. The device of claim 20 wherein said at least one elongated strut comprises a wire having a circular cross section of approximately 0.009 inches in diameter.

27. The device of claim 20 wherein said at least one elongated strut comprises a wire having a rectangular cross section of approximately 0.007 inches by approximately 0.009 inches.

28. The device of claim 20 wherein said flexural hinge points comprise coiled portions of the elongated strut.

29. The device of claim 28 wherein said coiled portions have an inner diameter of approximately 0.010–0.025 inches.

30. The device of claim 28 wherein said coiled portions have an inner diameter of approximately 0.016 inches.

31. The device of claim 28 wherein said coiled portions include at least two coils.

32. The device of claim 28 wherein said coiled portions include at least three coils.

33. The device of claim 20 wherein said alloy comprises approximately 35% nickel, 35% cobalt, 20% chromium and 9.75% molybdenum.

34. The device of claim 20 wherein said alloy further comprises manganese, carbon, beryllium and iron.

35. The device of claim 34 wherein said alloy comprises at least approximately 14% nickel, 39% cobalt, 19% chromium, 6% molybdenum and 1.5% manganese.

36. The device of claim 35 wherein said alloy further comprises up to approximately 0.15% carbon and 0.1% beryllium.

37. The device of claim 20 wherein said wire has been cold-worked to reduce its cross-sectional area by approximately 30–80%.

38. The device of claim 20 wherein said annealing is carried out at temperature between approximately 450°–1000° F.

39. A device for percutaneous transluminal repair of septal detects comprising:

a first occluder having an initial cross sectional configuration smaller than that of the defect to be repaired and a second expanded configuration larger than that of the defect;

a second occluder having an initial cross sectional configuration smaller than that of the defect to be repaired and a second expanded configuration larger than that of the defect; and a connector for fastening the first occluder to the second occluder;

each of the first occluder and second occluder comprising a framework having a central hub with a plurality of elongated struts radiating therefrom;

each of said elongated struts further including three flexural hinge points and an end loop, said flexural hinge points including a shoulder flexural hinge point, an elbow flexural hinge point and a flexural hinge point between the elbow flexural hinge point and the end loop.

40. The device of claim 39 wherein said means comprises elongated struts comprise a wire having a square, round, rectangular, trapezoidal or triangular cross section.

41. The device of claim 40 wherein said cross section is approximately 0.005–0.015 inches.

42. The device of claim 40 where said elongated struts comprise a wire having a square cross section of approximately 0.008 inches.

43. The device of claim 40 wherein said elongated struts comprise a wire having a circular cross section of approximately 0.009 inches in diameter.

44. The device of claim 40 wherein said elongated struts comprise a wire having a rectangular cross section of approximately 0.007 inches by approximately 0.009 inches.

45. The device of any one of claims 40 to 44 wherein said flexural hinge points comprise coiled portions of the elongated strut.

46. The device of claim 45 wherein said coiled portions have an inner diameter of approximately 0.010–0.025 inches.

47. The device of claim 45 wherein said coiled portions have an inner diameter of approximately 0.016 inches.

48. The device of claim 45 wherein said coiled portions include at lest two coils.

49. The device of claim 40 wherein said elongated struts comprise a wire fabricated of a metallic alloy containing nickel, cobalt, chromium and molybdenum.

50. The device of claim 49 wherein said alloy comprises approximately 35% nickel, 35% cobalt, 20% chromium and 9.75% molybdenum.

51. The device of claim 49 wherein said alloy further comprises manganese, carbon, beryllium and iron.

52. The device of claim 51 wherein said alloy comprises at least approximately 14% nickel, 39% cobalt, 19% chromium, 6% molybdenum and 1.5% manganese.

53. The device of claim 52 wherein said alloy further comprises up to approximately 0.15% carbon and 0.1% beryllium.

54. The device of claim 49 wherein said alloy is annealed to a degree sufficient to cause precipitation hardening thereof.

55. The device of claim 54 wherein said annealing is carried out at a temperature between approximately 450°–1000° F.

56. The device of claim 49 wherein said wire has been cold-worked to reduce its cross-sectional area by approximately 30–80%.

57. A device for percutaneous transluminal repair of septal detects comprising:

a first occluder having an initial cross sectional configuration smaller than that of the defect to be repaired and a second expanded configuration larger than that of the defect;

a second occluder having an initial cross sectional configuration smaller than that of the defect to be repaired and a second expanded configuration larger than that of the defect; and a connector for fastening the first occluder to the second occluder;

each of the first occluder and second occluder comprising a framework having a central hub with a plurality of elongated struts radiating therefrom;

the framework fabricated of a wire having a square, rectangular, round, trapezoidal or triangular cross section;

each of said elongated struts further including three flexural hinge points and an end loop, said flexural hinge points including a shoulder flexural hinge point, an elbow flexural hinge point and a flexural hinge point between the elbow flexural hinge point and the end loop.

58. The device of claim 57 wherein said cross section is approximately 0.005–0.015 inches on edge.

59. The device of claim 57 wherein said at least one elongated strut comprises a wire having a square cross section of approximately 0.008 inches on edge.

60. The device of claim 57 wherein said at least one elongated strut comprises a wire having a circular cross section of approximately 0.009 inches in diameter.

61. The device of claim 57 wherein said at least one elongated strut comprises a wire having a rectangular cross section of approximately 0.007 inches by approximately 0.009 inches.

62. The device of claim 61 wherein said coiled portions have an inner diameter of approximately 0.010–0.025 inches.

63. The device of claim 57 wherein said flexural hinge points comprise coiled portions of the elongated strut.

64. The device of claim 63 wherein said coiled portions have an inner diameter of approximately 0.016 inches.

65. The device of claim 63 wherein said coiled portions include at least two coils.

66. The device of claim 63 wherein said coiled portions include at least three coils.

67. A device for percutaneous transluminal repair of septal defects comprising:

a first occluder having an initial cross sectional configuration smaller than that of the defect to be repaired and a second expanded configuration larger than that of the defect;

a second occluder having an initial cross sectional configuration smaller than that of the defect to be repaired and a second expanded configuration larger than that of the defect; and a connector for fastening the first occluder to the second occluder;

each of the first occluder and second occluder comprising a framework having a central hub with a plurality of elongated struts radiating therefrom;

the framework fabricated of a wire having a metallic alloy composition comprising nickel, cobalt, chromium and molybdenum;

each of said elongated struts further including three flexural hinge points, wherein at least one of said struts has at least one end loop, said flexural hinge points including a shoulder flexural hinge point, an elbow flexural hinge point and a flexural hinge point located between the end loop and the elbow flexural hinge point.

68. The device of claim 67 wherein the metallic alloy composition is annealed to a degree sufficient to cause precipitation hardening thereof.

69. The device of claim 68 wherein said annealing is carried out at a temperature between approximately; 450°–1000° F.

70. The device of claim 67 wherein the metallic alloy composition comprises an alloy selected from the group consisting of MP35N and Elgiloy.

71. The device of claim 67 wherein the flexural hinge points comprise coiled portions of the elongated strut.

72. The device of claim 71 wherein the metallic alloy composition comprises an alloy selected from the group consisting of MP35N and Elgiloy.

73. The device of claim 71 wherein said coiled portions have an inner diameter of approximately 0.010–0.025 inches.

74. The device of claim 71 wherein said coiled portions have an inner diameter of approximately 0.016 inches.

75. The device of claim 71 wherein said coiled portions include at least two coils.

76. The device of claim 71 wherein said coiled portions include at least three coils.

77. The device of claim 67 wherein said wire has been cold worked to reduce its cross-sectional area by approximately 30–80%.

78. The device of claim 67 wherein said alloy further comprises manganese, carbon, beryllium and iron.

79. The device of claim 78 wherein said alloy comprises at least approximately 14% nickel, 39% cobalt, 19% chromium, 6% molybdenum and 1.5% manganese.

80. The device of claim 79 wherein said alloy further comprises up to approximately 0.15% carbon and 0.1% beryllium.

* * * * *

UNITED STATES PATENT AND TRADEMARK OFFICE
CERTIFICATE OF CORRECTION

PATENT NO.  : 5,425,744
DATED       : June 20, 1995
INVENTOR(S) : Fagan, et als.

It is certified that error appears in the above-indentified patent and that said Letters Patent is hereby corrected as shown below:

Claim 48, col. 12, line 38, change "lest" to ---least---.

Claim 57, col. 12, line 64, change "detects" to ---defects---.

Signed and Sealed this

Twenty-first Day of November, 1995

*Attest:*

BRUCE LEHMAN

*Attesting Officer*       *Commissioner of Patents and Trademarks*